United States Patent [19]

Zoller et al.

[11] 4,144,260
[45] Mar. 13, 1979

[54] PRODUCTION OF ALUMINUM SALTS OF N-NITROSO-N-ALKYL-HYDROXYLAMINES

[75] Inventors: Karl Zoller, Ludwigshafen; Dietmar Werner, Weisenheim; Eberhard Auer, Mutterstadt, all of Fed. Rep. of Germany

[73] Assignee: BASF Aktiengesellschaft, Ludwigshafen, Fed. Rep. of Germany

[21] Appl. No.: 563,225

[22] Filed: Mar. 28, 1975

[30] Foreign Application Priority Data

Apr. 30, 1974 [DE] Fed. Rep. of Germany ....... 2420874

[51] Int. Cl.² ............................................... C07F 5/06
[52] U.S. Cl. ......................... 260/448 R; 260/583 DD; 260/563 C; 423/267
[58] Field of Search ....... 260/448 R, 583 DD, 563 C; 423/267

[56] References Cited

U.S. PATENT DOCUMENTS 3,480,653  11/1969  Pande et al. .................... 260/448 R

FOREIGN PATENT DOCUMENTS 815537  6/1959  United Kingdom.

OTHER PUBLICATIONS

Morton, "Laboratory Methods in Organic Chemistry", McGraw Hill, N.Y., N.Y., 1938, pp. 195–197.
Welcher, "Organic Analytical Reagents," vol. III, D. Von Nostrand, N.Y., 1947, pp. 355, 394, 395.
Kirk–Othmer, "Encyclopedia of Chemical Technology," vol. 8, 1965, pp. 719–720.

*Primary Examiner*—Arthur P. Demers
*Attorney, Agent, or Firm*—Keil & Witherspoon

[57] ABSTRACT

Aluminum salts of N-nitroso-N-alkylhydroxylamines are produced by the reaction of an aluminum salt with an alkali metal salt, alkaline earth metal salt and/or ammonium salt of an N-nitroso-N-alkylhydroxyl-amine and/or the aftertreatment of an appropriate aluminum salt in the presence of water and an organic solvent. The products have fungicidal properties and are starting materials for the production of fungicides for wood preservatives, colored surface coatings, synthetic resins and dye formulations.

10 Claims, No Drawings

PRODUCTION OF ALUMINUM SALTS OF N-NITROSO-N-ALKYL-HYDROXYLAMINES

This application discloses and claims subject matter described in German Patent Application P No. 24 20 874.0, filed Apr. 30, 1974, which is incorporated herein by reference.

The invention relates to a process for the production of aluminum salts of N-nitroso-N-alkylhydroxylamines by the reaction of an aluminum salt with an alkali metal salt, alkaline earth metal salt and/or ammonium salt of an N-nitroso-N-alkylhydroxylamine and/or the aftertreatment of an appropriate aluminum salt in the presence of water and an organic solvent.

It is known from German Pat. No. 1,019,657 that an ammonium salt of N-nitroso-N-cyclohexylhydroxylamine can be reacted with an inorganic aluminum salt in aqueous solution to give N-nitroso-N-cyclohexylhydroxylamine aluminum. It is stated in the specification that the salts are reacted with each other at ambient temperature. The reaction gives a highly contaminated end product which because of its low melting point is obtained as an elastomeric tacky material. The impurities are difficult, troublesome and expensive to separate by repeated recrystallization of the salt; an aggravating factor is the time-consuming drying of the finely crystalline product thus obtained and the difficulty in handling large amounts of fine dusty crystalline substance. The impurities contain a large proportion of aluminum hydroxide, hydrated aluminum oxide, unreacted starting materials and possibly partly hydrolyzed inorganic aluminum salts. In the further processing of the end product the impurities contaminate the secondary products and impair their color and yield.

The object of the invention is to provide a new process for producing aluminum salts of N-nitroso-N-alkylhydroxylamines in higher purity and better yield more simply and more economically.

We have found that an aluminum salt of an N-nitroso-N-alkylhydroxylamine of the formula:

in which R is alkyl or cycloalkyl, can be obtained advantageously by the reaction of an aluminum salt with an alkali metal salt, alkaline earth metal salt and/or ammonium salt of an N-nitroso-N-alkylhydroxylamine (I) in the presence of water by carrying out the reaction and/or the aftertreatment of the aluminum salt of an N-nitroso-N-alkylhydroxylamine (I) in the presence of water, an acid and an organic solvent which is inert under the reaction conditions.

We have further found that it is advantageous to use an alkali metal salt of N-nitroso-N-cyclohexylhydroxylamine as the starting material.

We have found moreover that it is advantageous to use aromatic or araliphatic hydrocarbons as organic solvents.

We have also found that it is advantageous to separate the aqueous phase from the mixture after the reaction or aftertreatment is over and to separate the organic solvent from the organic phase by distillation.

When aluminum sulfate and potassium N-nitroso-N-cyclohexylhydroxylamine are used the reaction may be represented by the following equation:

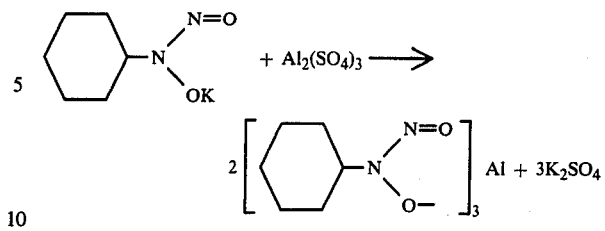

The process according to the invention gives aluminum salts of N-nitroso-N-alkylhydroxylamines in better purity and better yield more simply and more economically than prior art methods. Expensive and troublesome purification operations on the end product and also on the secondary products are not necessary. Further processing of the end product is facilitated and the quality of the secondary products in color, purity and in some cases in yield is improved. When after the end of the reaction the aqueous phase formed is separated and the organic phase is distilled, the end product, particularly the aluminum N-nitroso-N-cyclohexylhydroxylamine remains after cooling as distillation residue surprisingly in a particularly advantageous vitreous, brittle, very dry amorphous form. This form of the end product obtained in this manner permits the handling, processing and transportation of large amounts of aluminum salt of N-nitroso-N-alkylhydroxylamine without waste or disturbances. Difficulties also are not encountered in drying. Because of the consequent avoidance of large amounts of dust in the surrounding atmosphere and in the offgas, the process of the invention is more favorable environmentally, more hygienic and involves less health hazards for operatives.

It is surprising having regard to the prior art that the end product according to the invention is not obtained in crystalline form (which was to be expected in the case of a purified organic aluminum salt) but by a simple and economical method a vitreous form which is particularly easy to handle.

The aluminum salt is advantageously reacted in a stoichiometric proportion with the N-nitroso-N-alkylhydroxylamine salt; either salt may be used in an excess of up to 1 mole over the stoichiometric amount in relation to the other salt. The salt of the N-nitroso-N-alkylhydroxylamine (basic salt) used may be an alkali metal salt, preferably the sodium or potassium salt; an alkaline earth metal salt, preferably the magnesium or calcium salt; or an ammonium salt in the form of a salt of the N-nitroso-N-alkylhydroxylamine with ammonia or a primary, secondary or tertiary amine; examples of such ammonium salts are the salts of an N-nitroso-N-alkylhydroxylamine with ammonia, trimethylamine, triethylamine, pyridine, diethylaniline, dimethylaminoethanol, N-ethylpiperidine, N-methylpyrrolidine, ethylamine, diethylamine, aniline, N-methylaniline, benzylamine, cyclohexylamine, di-tert.-butylamine, isopropylamine, ethylaniline, diphenylamine, dimethylamine, diisopropylamine, triethanolamine, toluidine, dimethylaniline, cyclopentylamine, dicyclohexylamine, triphenylamine, α-naphthylamine, β-naphthylamine, pyrrole, pyrazole, imidazole, piperidine, quinoline, morpholine, isoquinoline, laurylamine, stearylamine, butylamine, dibutylamine, tributlyamine, amylamine, diamylamine, triamylamine, piperazine, N,N-dimethyl-N-laurylamine, N,N'-dimethyl-N-stearylamine, ethanolamine, diethanolamine, pyrrolidone, imidazoline, pyrimidine, propylamine, dipropylamine, tripropylamine, tert.-butylamine, dibenzylamine, tribenzylamine, tricyclohexylamine, N-methyl-N-ethylamine, mono-m-chlorophenylamine, mono-o-chlorophenylamine, mono-p-chlorophenylamine, di-m-chlorophenylamine, di-o-chlorophenylamine, di-p-chlorophenylamine, tri-m-chlorophenylamine, tri-o-chlorophenylamine, tri-p-chlorophenylamine, m-ethoxyphenylamine, o-ethoxyphenylamine, p-ethoxyphenylamine, di-m-ethoxyphenylamine, di-o-ethoxyphenylamine, di-p-ethoxyphenylamine, tri-m-ethoxyphenylamine, tri-o-ethoxyphenylamine, tri-p-ethoxyphenylamine, nitrophenylamine, di-(nitrophenyl)amines, tri-(nitrophenyl)-amines and hexamethylenimine.

Sodium salts, potassium salts and ammonium salts devoid of substituents on the nitrogen atom are particularly advantageous. Preferred hydroxylamines of the abovementioned salts and consequently preferred hydroxylamines (I) contained in the end products are those in whose formulae R is alkyl of one to ten and particularly one to four carbon atoms or cycloalkyl of five to seven carbon atoms. N-nitroso-N-cyclohexylhydroxylamine is particularly preferred. Other suitable hydroxylamines (I) are: N-methyl-N-nitrosohydroxylamine, N-isopropyl-N-nitrosohydroxylamine,
N-ethyl-N-nitrosohydroxylamine,
N-tert.-butyl-N-nitroso-hydroxylamine,
N-n-butyl-N-nitrosohydroxylamine,
N-hexyl-N-nitrosohydroxylamine,
N-decyl-N-nitrosohydroxylamine,
N-cyclopentyl-N-nitrosohydroxylamine and
N-cycloheptyl-N-nitrosohydroxylamine.

Organic or inorganic aluminum salts are suitable. It is preferred to use aluminum chloride and particularly aluminum sulfate. Other suitable salts are the bromides, fluorides, phosphates, nitrate, carbonates, iodides or aluminum salts of organic acids such as acetic acid, formic acid or of sulfonic acids, for example benzenesulfonic acid or p-toluenesulfonic acid, of oxalic acid, benzoic acid, propionic acid, butyric acid or glycollic acid. Compounds may also be used which have been formed by the reaction of such aluminum salts, for example aluminum oxide, aluminum hydroxide, aluminum complex compounds, for example with 1,3-diketones such as acetylacetone, benzolacetone, and β-ketocarboxylic esters such as acetylacetic esters, aluminum alcoholates such as the isopropylate, tert.-butylate, hydrated aluminum oxide, aluminates in an appropriate acid reaction medium, for example in the presence of the abovementioned acids.

The reaction is generally carried out at a temperature of from 10° to 150° C., preferably from 25° to 120° C. and particularly from 30° to 100° C., at atmospheric or superatmospheric pressure, for example a pressure of from 750 mm Hg to 10 atmospheres, continuously or batchwise. It is convenient to use a total amount of water sufficient to dissolve the starting salts or a larger amount in relation to the solubility of the salts. The reaction is preferably carried out with a ratio of from 1 to 1000 and particularly from 50 to 300% by weight of water based on organic solvent and with a total amount of liquid of from 10 to 100,000 and particularly from 100 to 10,000% by weight based on the aluminum salt of N-nitroso-N-alkylhydroxylamine to be prepared (the end product being calculated in a theoretical yield of 100%). By total amount of liquid we mean the total amount of water and organic solvent added to the starting mixture not including water of crystallization and the water absorbed onto the salt and introduced with the salt. The organic solvent inert under the reaction conditions is advantageously a solvent having little or no miscibility with water. Convenient solvents are: aromatic, araliphatic, aliphatic and cycloaliphatic hydrocarbons such as benzene, toluene, xylene, ligroin, hexane, pentane, heptane, cyclohexane, trimethylbenzene, methylpropylbenzene, dimethylethylbenzene, tetramethylbenzene and cyclooctane; chlorohydrocarbons such as carbon tetrachloride, chloroform, methylene chloride and chlorobenzene; ethers such as diethyl ether and dipropyl ether; esters such as ethyl acetate and butyl acetate; ketones such as dilauryl ketone, distearyl ketone, ethylmethyl ketone and cyclohexanone; and appropriate mixtures; nitroaromatic compounds, for example nitrobenzene and o-nitrotoluene; and aromatic nitriles such as benzonitrile and m-chlorobenzonitrile. Particularly preferred are aromatic hydrocarbons and mixtures thereof, for example the abovementioned alkylbenzenes, particularly with one to four carbon atoms in the side chain such as mixtures of trimethylbenzene, methylpropylbenzene, dimethylethylbenzene and tetramethylbenzene, for example with proportions by weight of from 10 to 60% by weight of each component based on the whole mixture.

The reaction is carried out in the presence of an acid, advantageously in an amount of from 0.001 to 1 and particularly from 0.01 to 0.5 mole of acid based on the basic starting salt of N-nitroso-N-alkylhydroxylamine. Inorganic or organic acids may be used. Instead of a monobasic acid it is also possible to use an equivalent amount of a polybasic acid. The following are examples of suitable acids: hydrogen chloride, hydrogen bromide, hydrogen iodide, perchloric acid, sulfuric acid, phosphoric acid and nitric acid; sulfonic acids such as benzenesulfonic acid and p-toluenesulfonic acid; acids containing boron such as boric acid and fluoboric acid; aliphatic carboxylic acids such as chloroacetic acid, dichloroacetic acid, trichloroacetic acid, acrylic acid, oxalic acid, cyanoacetic acid, acetic acid, tartaric acid, citric acid, caprylic acid, trimethylacetic acid, β-chloropropionic acid, succinic acid, malonic acid, isovaleric acid, valeric acid, glutaric acid, adipic acid and maleic acid; cycloaliphatic, araliphatic and aromatic carboxylic acids such as benzoic acid, phenylpropionic acid, cyclohexanoic acid, phenylacetic acid, phthalic acid, p-toluic acid and p-nitrobenzoic acid; acid ion exchangers; heterocyclic carboxylic acids such as imidazole-4-carboxylic acid, nicotinic acid, pyrazine carboxylic acid, pyridine-o-carboxylic acid, quinoline-2-carboxylic acid and pyrrole-2-carboxylic acid; or appropriate mixtures. The acids may be used in concentrated form, mixed with one another and/or mixed with one of the abovementioned solvents and particularly water. The aluminum salt and the acid are preferably chosen so that the anion of the salt corresponds to the acid. The preferred acids are therefore those which contain the anions of the abovementioned aluminum salts and particularly hydrochloric and sulfuric acids.

The reaction may be carried out as follows: a mixture of the starting salt with an acid, water and the organic solvent is kept for from 36 seconds to 1 hour at the reaction temperature. The starting salt is conveniently added in the form of an aqueous solution. The reaction mixture is then cooled if necessary and processed in the usual way, for example by separating the organic phase from the aqueous phase by allowing the organic phase to settle or by centrifuging. The organic phase is dried by a conventional method, for example by distilling the solution or by adding a drying agent such as sodium sulfate, magnesium sulfate, sodium carbonate or calcium chloride. When a high boiling point solvent is used it may be advantageous to add a low boiling point solvent, for example benzene, chloroform or pentane by means of which residual water may be removed by azeotropic distillation. The aluminum salt obtained as end product is usually further processed or supplied for use in the form of its solution, for example the solution obtained in the manner described above.

In a preferred embodiment the solvent is distilled off from the organic phase which has conveniently been dried, for example from a stirred vessel or circulation evaporator. It is advantageous to use a distillation plant in which the residence time of the end product is short, for example a thin-film or falling film evaporator. Distillation may be continuous or batchwise, at atmospheric or subatmospheric pressure, for example at from 760 to 1 mm Hg and at a temperature of from 30° to 200° C. and preferably from 50° to 180° C. In a particularly preferred embodiment the distillation is carried out at atmospheric pressure while passing through an inert gas, conveniently nitrogen, carbon dioxide and advantageously steam, for example in a falling film evaporator. The amount of inert gas is advantageously from 100 to 2000% by weight based on the solution to be distilled. The hot, viscous and clear residue is conveniently discharged by a pump. The molten N-nitroso-N-alkylhydroxylamine aluminum salt, preferably the N-cyclohexyl compound, is allowed to solidify in suitable molds or containers into a vitreous, brittle, amorphous substance. The end product may advantageously be pelleted and cooled in cooling baths, on cooling rollers or cooling conveyors. The cooled melt is conveniently comminuted or ground in conventional apparatus, for example crushers or mills and if necessary screened. The very pure amorphous end product thus obtained may be immediately further processed or transported to the place of use.

The process according to the invention is preferably carried out in the reaction of the basic salt of an N-nitroso-N-alkylhydroxylamine with an aluminum salt. The aluminum salt may be prepared however in another way, for example in a purely aqueous phase at low temperature according to the method described in German Patent No. 1,019,657, the salt isolated and treated in a mixture of water, acid and organic solvent, conveniently at the above-mentioned temperatures, reaction conditions and relative proportions of solvent and acid, for example for from 36 seconds to one hour, and the end product isolated from the mixture, for example in the manner described above. Similarly to the aqueous reaction mixture of a reaction of aluminum salt and basic salt of an N-nitroso-N-alkylhydroxylamine there may be added acid and organic solvent, conveniently in amounts corresponding to the abovementioned proportions, the mixture kept at the said reaction temperature for another 36 seconds to 1 hour and the end product isolated from the mixture in the said manner. In the two last mentioned embodiments the process according to the invention serves for the treatment and purification of the crude aluminum salt of an N-nitroso-N-alkylhydroxylamine. In the aftertreatment of the end product according to the invention the aluminum salt of the N-nitroso-N-alkylhydroxylamine is also preferably obtained as a distillation residue of the organic phase in an advantageous form.

Aluminum salts of N-nitroso-N-alkylhydroxylamines which can be prepared according to the process of the invention have fungicidal properties and are valuable starting materials for the production of fungicides for wood preservatives, colored surface coatings, synthetic resins and dye formulations. They are stabilizers for plastics, particularly in the production of unsaturated polyester resins and polyamide materials. Reference may be made to the abovementioned Patent for details of use.

The following Examples illustrate the invention. The parts set out in the following Examples are by weight. They bear the same relation to parts by volume as the kilogram to the liter.

EXAMPLE 1

113 parts of N-nitroso-N-cyclohexylhydroxylamine sodium salt is dissolved in 515 parts of water and mixed with 216 parts of a mixture of alkylbenzenes which is available commercially under the registered Trade Mark SHELLSOL AB. The mixture is heated to 60° C. and while stirring a solution of 75 parts of $Al_2(SO_4)_3.18H_2O$ in 240 parts of water and a solution of 6.75 parts of $H_2SO_4$ in 20.25 parts of water are added. After all has been added the mixture is stirred for fifteen minutes and cooled to 35° C. The mixture is allowed to settle for fifteen minutes and the aqueous phase is separated. The organic phase has 1 part of $Na_2SO_4$ and 1.5 parts of $Na_2CO_3$ added to it and after fifteen minutes the mixture is filtered. 320 parts of a 30% by weight solution of N-nitroso-N-cyclohexylhydroxylamine aluminum salt is obtained as filtrate in a mixture of alkylbenzene obtainable commercially under the trade mark SHELLSOL AG. The end product may be further processed in this form.

The organic solvent is distilled off from the organic phase at a boiling point of from 80° to 120° C. at 10 mm. The residue solidifies into a vitreous, amorphous material. 96 parts (99% of theory) of N-nitroso-N-cyclohexylhydroxylamine aluminum salt having a melting point of 75° to 90° C. is obtained.

EXAMPLE 2

6.3 parts of N-nitroso-N-cyclohexylhydroxylamine potassium salt is dissolved in 30 parts of water and mixed with 20 parts of toluene. The mixture is heated to 60° C. and while stirring a solution of 4.2 parts of $Al_2(SO_4)_3.18H_2O$ in 13 parts of water and a solution of 0.4 part of $H_2SO_4$ in 1.2 parts of water are added. After all has been added the mixture is stirred for fifteen minutes. It is allowed to settle for another fifteen minutes and the aqueous phase is separated. The solvent is distilled off from the organic phase at 10 mm and 150° C. in a falling film evaporator. The end product is obtained as the distillation residue in the form of a clear melt which solidifies into a solid, vitreous, amorphous material. The yield is 5.2 parts of N-nitroso-N-cyclohexylhydroxylamine aluminum salt (99% of theory) having a melting point of from 75° to 90° C.

EXAMPLE 3

Reaction and distillation are carried out analogously to Example 2, distillation being carried out at 130° C. and 760 mm in a Sambay evaporator. The feed of 30% by weight solution of the end product in toluene is 100 parts per second. 240 parts by volume of nitrogen is passed per hour through the evaporator countercurrent. 5.25 parts of N-nitroso-N-cyclohexylhydroxylamine aluminum salt is obtained having a melting point of 75° to 90° C. The yield is practically quantitative.

We claim:

1. A process for the production of the aluminum salt of an N-nitroso-N-alkylhydroxylamine of the formula (I):

in which R is alkyl of 1 to 10 carbon atoms or cycloalkyl of 5 to 7 carbon atoms, by the reaction of an aluminum salt with an alkali metal salt, alkaline earth metal salt and/or ammonium salt of an N-nitroso-N-alkylhydroxyl-amine (I) wherein the reaction and/or the aftertreatment of the aluminum salt of N-nitroso-N-alkylhydroxylamine (I) is carried out in the presence of water, an acid and an organic solvent which is inert under the reaction conditions.

2. A process as claimed in claim 1 wherein an alkali metal salt of N-nitroso-N-cyclohexylhydroxylamine is used as the starting material.

3. A process as claimed in claim 1 wherein an aromatic or araliphatic hydrocarbon is used as the organic solvent.

4. A process as claimed in claim 1 wherein a halohydrocarbon, ester, ketone or ether is used as the organic solvent.

5. A process as claimed in claim 1 wherein the aqueous phase is separated from the mixture after the end of the reaction or aftertreatment and the organic solvent is separated from the organic phase by distillation.

6. A process as claimed in claim 1 wherein the starting material is the sodium, potassium, magnesium, calcium salt or a salt of the N-nitroso-N-alkylhydroxylamine with ammonia or primary, secondary or tertiary amine.

7. A process as claimed in claim 1 wherein the reaction and/or aftertreatment is carried out at a temperature of from 10° to 150° C.

8. A process as claimed in claim 1 wherein the reaction and/or aftertreatment is carried out at a temperature of from 25° to 120° C.

9. A process as claimed in claim 1 wherein the reaction an/or aftertreatment is carried out with a proportion of from 1 to 100% by weight of water based on organic solvent and with a total amount of liquid of from 10 to 100,000% by weight based on the aluminum salt of N-nitroso-N-alkylhydroxylamine to be prepared.

10. A process as claimed in claim 1 wherein the reaction and/or aftertreatment is carried out in the presence of an amount of from 0.001 to 1 mole of acid based on the starting salt of N-nitroso-N-alkylhydroxylamine.

* * * * *